United States Patent [19]

Pfeiffer et al.

[11] Patent Number: 4,878,234

[45] Date of Patent: Oct. 31, 1989

[54] DENTAL X-RAY DIAGNOSTICS INSTALLATION FOR PRODUCING PANORAMA SLICE EXPOSURES OF THE JAW OF A PATIENT

[75] Inventors: Joachim Pfeiffer; Werner Guenther; Manfred Muether; Erich Heubeck, all of Bensheim, Fed. Rep. of Germany

[73] Assignee: Siemens Aktiengesellschaft, Berlin and Munich, Fed. Rep. of Germany

[21] Appl. No.: 150,379

[22] Filed: Jan. 29, 1988

[30] Foreign Application Priority Data

Feb. 16, 1987 [DE] Fed. Rep. of Germany ....... 3704858

[51] Int. Cl.$^4$ .............................................. A61B 6/14
[52] U.S. Cl. .................................. 378/40; 250/370.09
[58] Field of Search ............................. 378/38, 39, 40; 250/370.9

[56] References Cited

U.S. PATENT DOCUMENTS

| 4,160,997 | 7/1979 | Schwartz | 358/111 |
| 4,188,537 | 2/1980 | Franke | |
| 4,239,971 | 12/1980 | Cushman | 378/39 |
| 4,298,800 | 11/1981 | Goldman | |
| 4,383,327 | 5/1983 | Kruger | |
| 4,492,869 | 1/1985 | Suzuki et al. | |

FOREIGN PATENT DOCUMENTS 0138625 4/1985 European Pat. Off. .

OTHER PUBLICATIONS

"Direct Soft X-Ray Response of a Charge-Coupled Image Sensor," Koppel, Rev. Sci. Instrum., vol. 48, No. 6, Jun. 1977, pp. 669–672.

Primary Examiner—Craig E. Church
Attorney, Agent, or Firm—Hill, Van Santen, Steadman & Simpson

[57] ABSTRACT

A dental x-ray diagnostics installation for producing panorama tomograms of the jaw of a patient has a radiation source and a detector, which converts x-radiation into corresponding light radiation, disposed on opposite sides of the patient. The detector is preceded by a secondary diaphragm. The radiation source, the detector and the secondary diaphragm are rotated around the patient so that radiation attenuated by the jaw, and passing through the secondary diaphragm is incident on the detector. At least one CCD sensor is provided on which light radiation generated by the detector is incident. The CCD sensor converts the light radiation into electrical signals. The sensor has an image zone with a number of lines parallel to a longitudinal extent of the opening of the secondary diaphragm, and has a storage zone. The lines in combination receive all of the light radiation so as to generate a complete charge image corresponding to the x-radiation incident on the detector. A clock generator is provided which controls transfer of the charge from the lines of the image zone into the storage zone, and also controls read-out of the storage zone. By selecting the frequency of the clock pulses generated by the clock pulse generator, the transfer and read-out speed can be selected to simulate the speed of movement of x-ray film in a conventional dental panorama tomography apparatus.

16 Claims, 5 Drawing Sheets

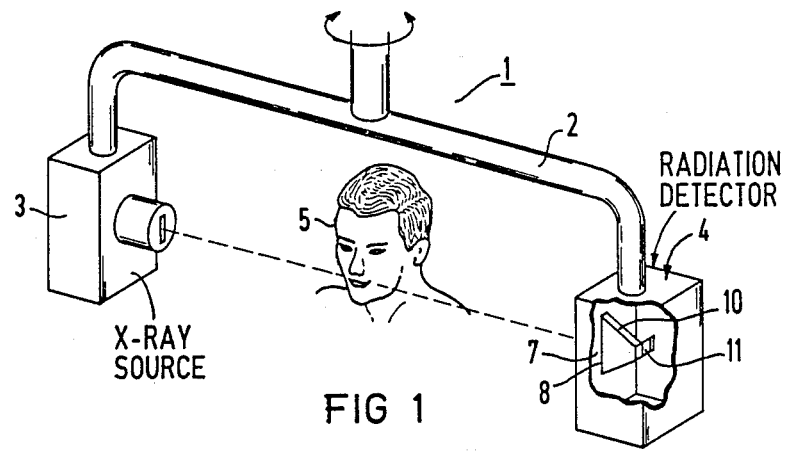
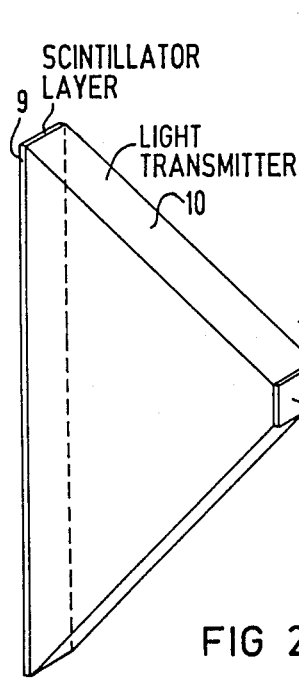
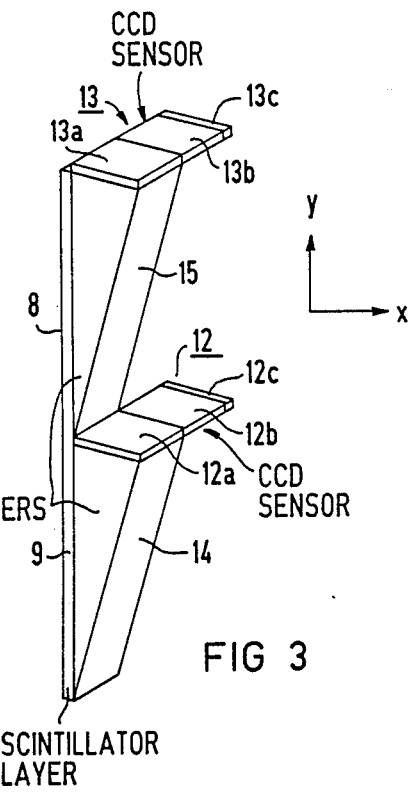

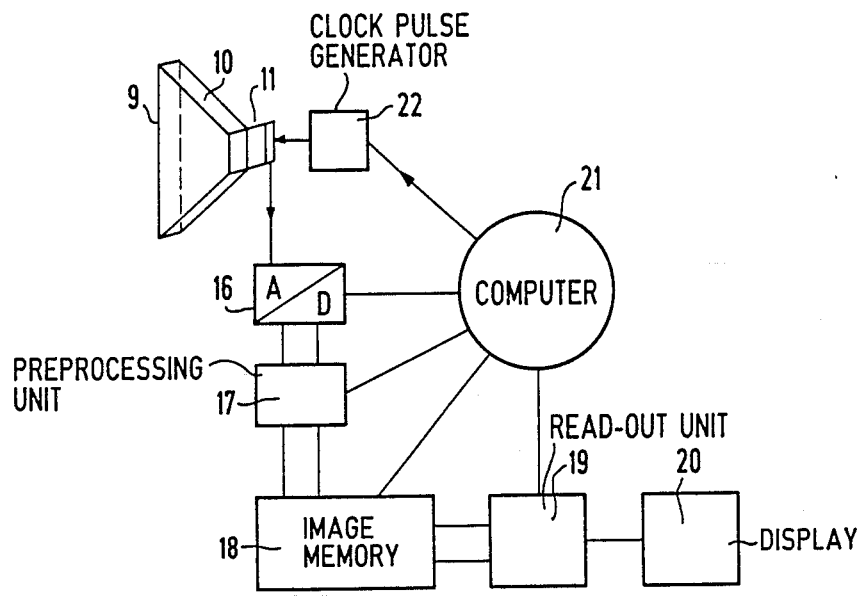
FIG 4
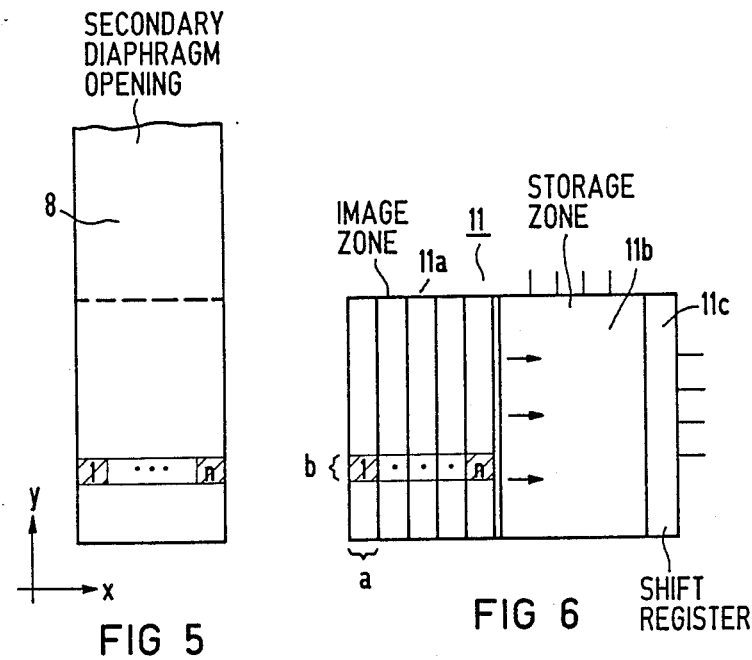
FIG 5
FIG 6

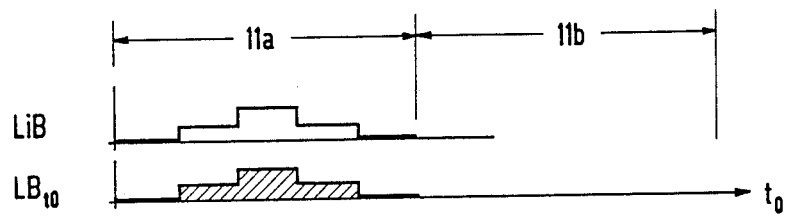
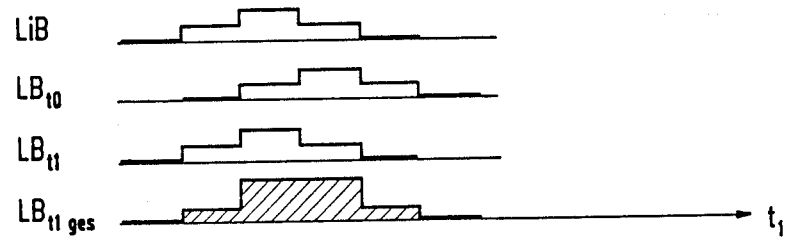
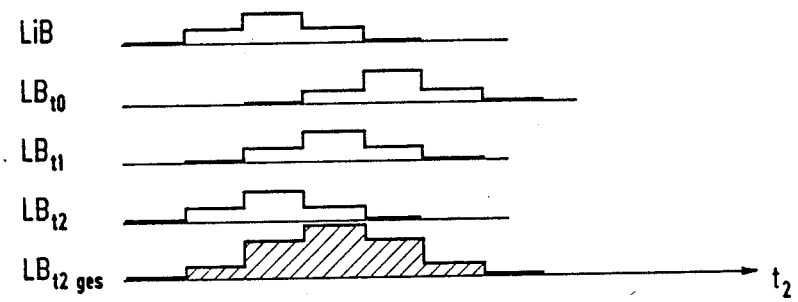
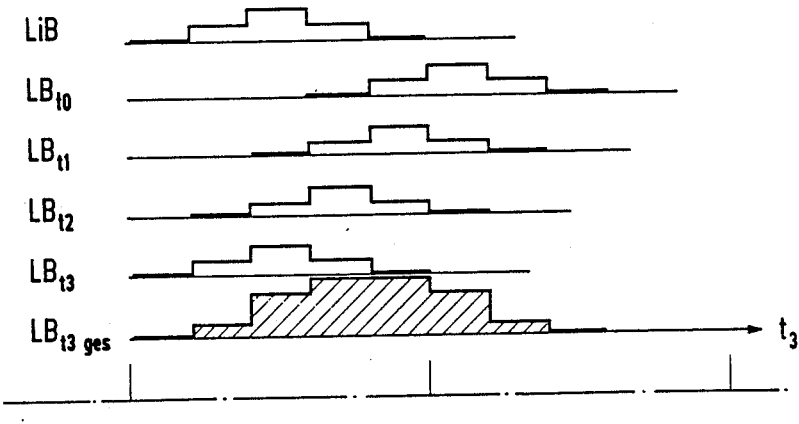
FIG 7A

DENTAL X-RAY DIAGNOSTICS INSTALLATION FOR PRODUCING PANORAMA SLICE EXPOSURES OF THE JAW OF A PATIENT

BACKGROUND OF THE INVENTION

1. Field of the Invention

The present invention is related to dental x-ray diagnostics installations for producing panorama tomograms of the jaw of a patient, and in particular to such an installation wherein the tomogram is electronically recorded in a manner which simulates recording on conventional moving x-ray film.

2. Related Application

The present application is related to another application entitled "Dental X-Ray Diagnostics Installation For Producing Panorama Slice Exposures Of The Jaw Of A Patient" (Werner Guenther, Manfred Muether, Erich Heubeck, Michael Doebert and Leonhard Werner) filed simultaneously herewith and having Ser. No. 140,123.

3. Description of the Prior Art

A dental x-ray diagnostics installation is described in German Patent No. 26 46 638, corresponding to U.S. Pat. No. 4,188,537. This installation includes a unit which is rotatable about a vertical axis which has an x-ray source and a secondary diaphragm, with a detector disposed behind the diaphragm. The carrier unit is rotated about the head of a patient as the patient is exposed to x-radiation, and the detector generates electrical signals proportional to the intensity of the radiation incident thereon. The electrical signals are supplied to an analog-to-digital converter, with the resulting digital signals being entered and stored in an image memory. A computer uses the stored data to calculate a complete image of the patient's jaw obtained during a full exposure, and the image is visually represented by an image reproduction means.

In the above-described known system, the panorama x-ray exposure can be electronically recorded and stored, instead of being recorded and stored in the conventional manner on x-ray film. This permits the image to be reproduced on a television monitor.

SUMMARY OF THE INVENTION

It is an object of the present invention to provide a dental panorama tomogram apparatus wherein an image of the jaw of a patient is electronically recorded in a manner which simulates recording of a similar image on moving x-ray film in a conventional apparatus.

The above object is achieved in a dental tomography apparatus having an x-ray source and a detector rotatable on a carrier around the head of a patient. A secondary diaphram is disposed in front of the detector, so that as the carrier rotates, radiation attenuated by the jaw of a patient, and passing through the opening of the secondary diaphragm, is incident on the detector. The detector converts the incoming x-radiation into corresponding light radiation. At least one CCD sensor is provided having an image zone to which the light radiation from the detector is coupled. The image zone has a plurality of lines disposed substantially parallel to the longitudinal extent of the secondary diaphragm opening. Charge is generated in these lines by the incoming light radiation, and is transferred to a storage zone of the CCD sensor. The lines in combination receive all of the light radiation to generate a complete charge image corresponding to the x-radiation incident on the detector. A clock pulse generator is provided which controls transfer of the charge from the lines into th storage zone, and also controls read-out of the storage zone. The speed of transfer and read-out are controlled by the clock pulse generator by selecting the frequency of the clock pulses such that the speed of a moving x-ray film in a conventional x-ray diagnostics installation is simulated.

DESCRIPTION OF THE DRAWINGS

FIG. 1 is a perspective view of an x-ray diagnostics installation constructed in accordance with the principles of the present invention.

FIG. 2 is a perspective view of a detector and sensor arrangement in accordance with the principles of the present invention using a single CCD sensor.

FIG. 3 is a perspective view of a detector and sensor arrangement constructed in accordance with the principles of the present invention using more than one CCD sensor.

FIG. 4 is a schematic block diagram of signal processing components in an x-ray diagnostics installation constructed in accordance with the principles of the present invention.

FIG. 5 is a front view of the opening of the secondary diaphragm in the installation constructed in accordance with the principles of the present invention showing a segment to explain the operation of the apparatus.

FIG. 6 is a plan view of a CCD sensor used in the apparatus constructed in accordance with the principles of the present invention segmented to explain the operation of the apparatus.

DESCRIPTION OF THE PREFERRED EMBODIMENTS

Figure 7B:
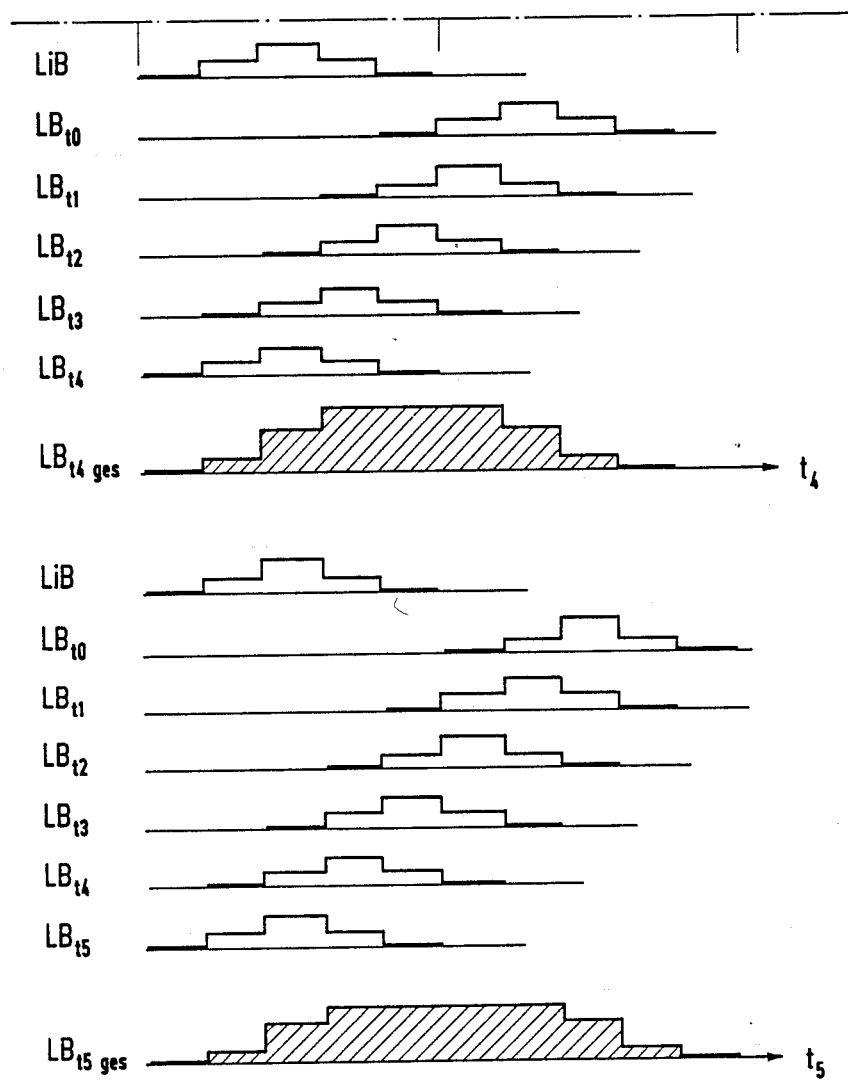
FIG. 7 (consisting of FIGS. 7A and 7B) is a series of voltage (charge)/time diagrams for explaining the operation of the apparatus constructed in accordance with the principles of the present invention.

The x-ray diagnostics installation shown in FIG. 1, constructed in accordance with the principles of the present invention, includes a rotary unit generally referenced at 1, consisting of an x-ray source 3 and a secondary diaphragm 7, with a detector arrangement 4 attached thereto, mounted at opposite ends of a carrier 2. The rotary unit 1 can be rotated around the head of a patient 5 in a known manner, as indicated by the arrow. Adjustment and control devices for rotating the unit 1 to generate a panorama tomogram of the jaw of the patient 5 are known to those skilled in the art, and need not be further described. It need only be noted that the head of the patient 5 is fixed in position with a mount (not shown) during an exposure, and the rotary unit 1 moves with a defined speed around the patient 5 given a prescribed exposure time. This movement is undertaken such that the x-ray emitted by the x-ray source 3 are always incident on the jaw of the patient 5 at substantially a right angle, and a substantially constant distances between the jaw and the detector 4 is maintained.

The secondary diaphragm 7 has a slot-like opening 8 having dimensions of, for example, 5×125 mm. The opening 8 is followed by means for converting the x-rays into visible light radiation. In the exemplary embodiment, a scintillator layer 9 having substantially the same dimensions as the opening 8 is provided for this purpose in the plane of the opening 8. The scintillator layer 9 is followed by an image transmission or coupling element 10, such as fiber optics, which reduces the format of the secondary diaphragm opening 8 to the format of the image zone of a CCD sensor 11. The image zone of the CCD sensor 11 has dimensions of, for example, 8×8 mm.

The CCD sensor 11 is of the type having an image zone 11a and a storage zone 11b disposed spatially separated on a chip, and having a shift register 11c coupled to the storage zone 11b. It is also possible, however, to use a CCD sensor of the type wherein the image and storage zones are disposed together within a chip.

To simplify the following description, it shall be assumed that the entire extent of the opening 8 in the secondary diaphragm 11 is imaged onto the surface of a single CCD sensor, as shown in FIG. 2. It is possible, however, to provide a plurality of such CCD sensors to cover the entirety of the opening 8, as shown in the embodiment of FIG. 3. In the embodiment of FIG. 3, two CCD sensors 12 and 13 are disposed at substantially a right angle relative to the plane of the opening 8, and two fiber optic elements 14 and 15 are provided as the transmission or coupling elements. The individual CCD sensors are of the same type as shown in FIG. 2, that is, with a storage zone spatially separated from an image zone, with a following shift register.

Processing of the electronic signals from the sensor 11 is undertaken using the components shown in FIG. 4. The output of the shift register 11c is supplied to an analog-to-digital converter 16, which is followed by a digital image processing system including a pre-processing unit 17, an image memory 18, an image read-out unit 19, a display 20, a computer 21 and a clocks pulse generator 22. Image data in the form of voltage signals generated by charge proportional to the x-ray intensity (in a manner described in detail below) are supplied at the output of the shift register 11c. These voltages are converted to digital signals in the converter 16. These digital values can then either be directly entered and stored in the image memory 18, or can be entered and stored in the image memory 18 after pre-processing in the unit 17. The computer 21 provides control (read-out) instructions required for this purpose through the clock pulse generator 22.

Direct entry of signals from the analog-to-digital converter 16 into the image memory 18 is preferable if the image memory 18 has a sufficiently large memory capacity, which can be justified given the constraints of cost and physical size. If direct entry is undertaken, the data are stored only during rotation of the rotary unit 1 which is necessary to complete an exposure, and after the conclusion of this exposure the data are processed, i.e., are added to generate a tomogram of the desired slice of the patient's jaw. Even though a relatively large amount of data must be processed for this purpose, this method has the advantage that a subsequent visual representation of a plurality of different slices is possible.

If, however, it is not economically justifiable to provide an image memory 18 having such a large memory capacity, the pre-processing unit 17 may be interposed between the converter 16 and the image memory 18, as indicated with dashed lines in FIG. 4. The pre-processing unit 17 includes an intermediate memory and a signal processor, by means of which the digital data from the converter 16 are added as a function of time based on a control instruction from the computer 21. This addition is undertaken to generate a tomogram of a desired slice of the patient's jaw. The processed data are subsequently forwarded to the image memory 18. An image memory 18 having a lower memory capacity can thus be used if the pre-processing unit 17 is present. If the pre-processing unit 17 is used, however, the slice or tomograph position (i.e., depth) is fixed, so that the slice position can not be varied within certain limits, as would be possible without the pre-processing unit 17, wherein the image data are not combined to form a tomogram until after a complete exposure.

A compromise solution is possible, however, wherein a plurality of adjacent image columns (i.e., data sets corresponding to successive positions of the secondary diaphragm 7, and thus of the opening 8 therein) are added as a function of time before storing this data, and the subsequent addition of these sum columns to form an image column is not undertaken until after storing the data. Using this method, the pre-processing unit 17 is not required to add all of the data, but only the data for a few adjacent columns. The data for these few columns are added as a function of time under the control of the computer 21, and are then forwarded to the image memory 18.

The creation of an image in the above-described apparatus shall be discussed below with reference to FIGS. 5 through 7.

The patient 5 is transradiated by a rectangular slot-shaped x-ray beam defined by a primary diaphragm (not shown) situated in the x-ray source 3. The radiation passes through the opening 8 of the secondary diaphragm 7 and is incident on the scintillator layer 9, wherein the x-radiation is converted into light radiation, to be registered by the CCD sensor 11. The signals registered by the CCD sensor 11 are proportional to the radiation intensity of the x-radiation attenuated by the patient 5.

In conventional tomographic techniques, an x-ray film to be exposed is moved at a defined speed behind the opening 8 of the secondary diaphragm 7, with the speed of film movement being a factor which defines the position (depth) of the tomographic slice. The position of the tomographic slice can thus be modified by varying the film speed. As described below, in the apparatus disclosed herein the x-ray film is replaced by an electronic detector arrangement, and the signals generated by the electronic detector arrangement are processed in a manner to generate a panorama tomogram corresponding to a tomogram produced using conventional moving film technology, but which can be reproduced on a television monitor.

The relationship between the opening 8 and the image zone 11a of the CCD sensor 11 shall first be described with reference to FIGS. 5 and 6. It is assumed that the opening 8 is imaged on the image zone of one or more such CCD sensors. The imaging relationship in the x-direction, i.e., perpendicular to the longitudinal extent of the opening 8, is defined by the ratio $1:n_x$, and by the ratio $1:n_y$ in the y-direction. Because the opening 8 has a width of about 5 mm, and currently available CCD sensors have an image zone width of 8 mm, $n_x = 1$ is applicable in the present context. Dependent on the number and size of image sensors employed, the imaging scale $n_y$ in the longitudinal (y) slot direction can be between 1 and about 20.

A picture element (pixel) on the CCD image zone surface having the dimensions a×b (a=row or line spacing, b=column spacing) corresponds to a pixel of $(n_x\cdot a)\times(n_y\cdot b)$ in the plane of the opening 8. In the simplified overview of FIGS. 5 and 6, 1 through n correspond to charge pixels in the CCD sensor, and also identify pixels in the direction of the longitudinal extent of the secondary opening 8. Accordingly, a line in this longitudinal direction of the secondary opening 8 is imaged on a CCD row or line.

By the application of clock pulses from the clock pulse generator 22, a charge image is transferred from the image zone 11a into the storage zone 11b, and is then read-out from the storage zone 11b via the shift register 11c, for supply to the analog-to-digital converter 16. During normal operation, i.e., in the standard clock sequence of a CCD sensor, the image integration time is approximately 20 ms. The image is clocked into the storage zone 11b in accord therewith. For this purpose, the same number of clock pulses as lines or rows of the CCD sensor is needed. Based on a CCD sensor type having 300 lines, and a clock period of 2 μs, the image zone 11a is thus emptied after about 0.6 ms, and can then immediately accept a new image. In conventional tomographic technology, the x-ray film is moved behind the secondary diaphragm opening at a defined speed so that the image data defined by the secondary opening are integrated over a defined time span during the movement of the film. This integration of the image data is electronically simulated in the present apparatus by clocking the charge image, generated by the action of the light radiation from the scintillator layer 9 on the surface of the CCD sensor 11, out of the image zone 11a into the storage zone 11b in a defined clock sequence, and then clocking the stored image out of the storage zone 11b line-by-line via the shift register 11c. The clock sequence is selected such that the charge image, referenced to the plane of the secondary opening 8, has the same speed in the x-direction which a moving x-ray film would have in conventional tomographic technology. The clock frequency thus has the following relationship to the equivalent speed v of a moving film:

$$f_{Takt} = \frac{v}{n_x \cdot a}$$

wherein $f_{Takt}$ is the number of lines per second and $(n_x\cdot a)$ is the CCD line spacing referenced to the plane of the secondary opening 8. Given a typical film speed of 30 mm/s and a line spacing of 20 μm, and based on an imaging ratio of 1:1 in the x-direction, a clock frequency of 1500 Hz results.

The procedure of image integration shall be described with reference to FIG. 7 (divided into FIG. 7A and 7B) for five of the pixels 1 ... n shown in FIGS. 5 and 6 for the points in time $t_o$ thru $t_5$. FIG. 7 shows the light image LiB for five pixels having different intensity I, and immediately below is shown the associated charge image LB arising in the image zone of the CCD sensor. It can be seen that a charge image corresponding to a defined "first" light pixel is present at time $t_o$. At time $t_1$, this charge image $LB_{to}$ is shifted in the x-direction, i.e., in the column direction, of the CCD sensor. At the same time, a new light pixel again becomes a charge pixel $LB_{t1}$. At time $t_2$, the charge images are again shifted in the x-direction. Integration of the individual charge images $LB_{to}$, $LB_{t1}$ ... yields the overall charge image $LB_{t1\,ges}$, $LB_{t2\,ges}$ ... respectively shown below for the points in time $t_1$ ... $t_5$. The light images which occur successively chronologically offset at the same location (the secondary opening) in the charge image are accordingly spatially offset and are added. This procedure corresponds precisely to the behavior of a moving film in conventional tomographic techniques. The spatially offset addition of the chronologically successive light images in the charge image is continued until the CCD line in question has reached the storage zone (see the charge image $LB_{to}$ at time $t_5$). When the line reaches the shift register 11c, it is serially clocked out, converted from analog form to digital form, and is entered into the image memory as a column.

It is also possible to add the charge of a number of CCD lines, and to enter this sum into the memory 18 as a column, as described above in connection with the operation of the preprocessing unit 17.

An alternative method for simulating the integration behavior f a moving film using a CCD sensor in accordance with the principles of the present invention is as follows.

The standard clock sequence of a CCD sensor, which is usually about 15 kHz, is modified such that the lines are shifted in the image zone 11a with a clock rate $f_{Takt}$ which corresponds to the film speed in conventional exposure techniques during the image integration time $t_{BA}$ of the CCD element. This image integration time may be, for example, 20 ns. During the image integration time $t_{BA}$, the charge image migrates between, for example, 0.1 and 1 mm within the image zone 11a. After the integration time $t_{BA}$, the entire image is shifted into the storage zone 11b with the highest clock rate which is compatible with the CCD element. This requires approximately 0.6 ms given roughly 300 CCD lines and a clock period of 2 μs. The next image pick-up time begins immediately thereafter. During this next pick-up time, the previous image is clocked out of the storage zone and the digitized data are added offset in the image memory 18. The image and storage zones can thus be differently clocked.

Further details are as follows. At time $t_o$, the image zone 11a is empty. A clock sequence having the frequency $$f_{Takt} = \frac{v}{n_x \cdot a}$$

is applied to the image zone. During the image integration time $t_{BA}$, the charge image is clocked out of the image zone 11a into the storage zone 11b. This requires the aforementioned time $t_v$ of, for example, 0.6 ms. After the charge image has been clocked out of the image zone and into the storage zone, the image zone is empty, and a clock sequence for transferring the data out of the storage zone is applied to the storage zone. This clock frequency is extremely high, and may be, for example, 15,000 lines/s. During this clocking-out procedure, a number of lines corresponding to $$\frac{P_x}{n_x \cdot a}$$

are summed, wherein $P_x$ is the extent of an image storage pixel in the x-direction referenced to the secondary slot plane. This sum line is entered in the image memory 18 as a column. This operation is periodically repeated.

An image as generated during each image integration time $t_{BA}$ occupies $$Z \cdot n_x \cdot \frac{a}{P_x}$$

columns in the image memory 18, wherein Z is the number of CCD lines. The addition of the individual images in the image memory 18 is undertaken with an offset $m_{BSS}$, this offset being the column number by which two successive images are stored (entered), and being defined by the relationship $$m_{BSS} = \frac{v \cdot (t_{BA} + t_v)}{P_x}.$$

An advantage of this second method is that disturbances which are produced by the dark current effect (the collection of charges in the image zone which are not caused by light radiation during the creation of th charge image) can be avoided.

As noted above, it is not yet possible, give the current state of the art, to obtain a single CCD sensor which would cover the standard dimensions of the secondary opening (5×120 mm) of conventional panorama tomogram devices. Commercially available, and thus relatively economical, CCD image sensors have formats on the order of magnitude of 7×9 mm, given 400 thus 600 pixels. Given the aforementioned dimensions of the secondary opening of 5×120 mm, and based on 50×1200 pixels, it is possible to cover the secondary opening by providing two such image sensors each having the dimensions 7×9 mm. It is necessary to correspondingly convert the format for this purpose.

Figure 8:
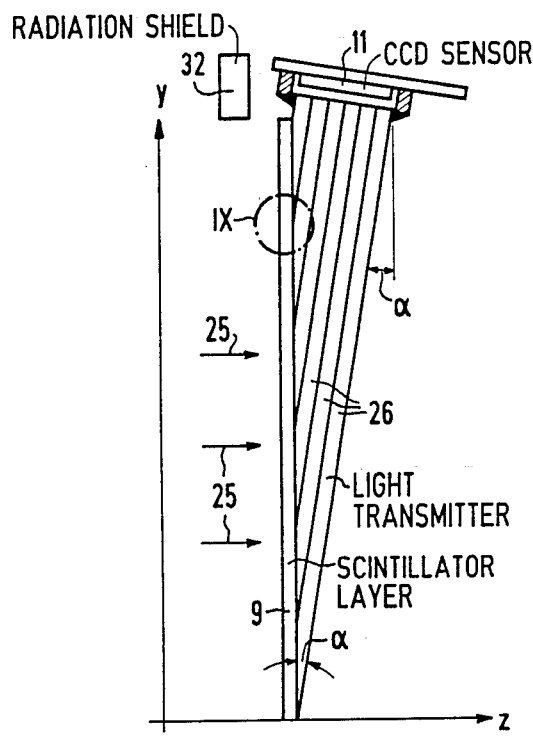
FIG. 8 is a plan view showing the spatial relationship between the detector and a CCD sensor in accordance with the principles of the present invention.
Figure 9:
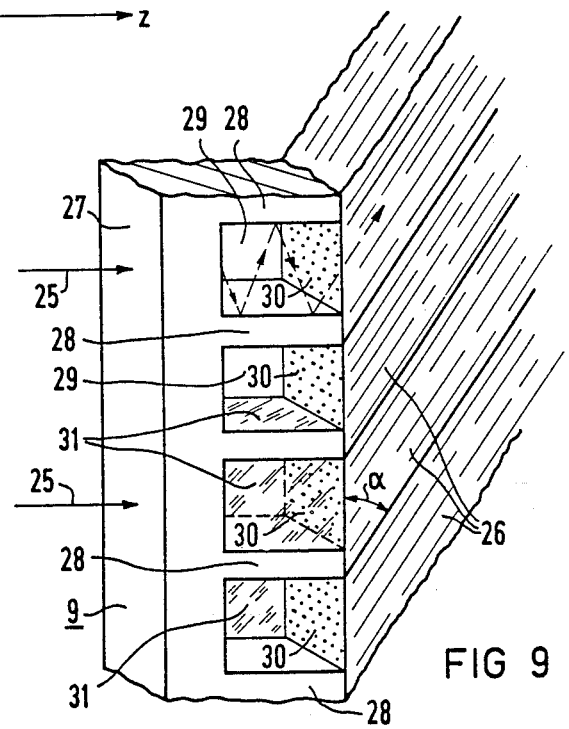
FIG. 9 is an enlarged perspective view of the portion of FIG. 8 indicated at XI.

A format converter is shown in FIGS. 8 and 9 wherein, as in FIG. 2, the format of the secondary opening 8 (corresponding in size to the scintillation layer 9) is to be imaged onto a single CCD sensor 11. The structure shown in FIGS. 8 and 9, however, applies by analogy to the embodiment of FIG. 3, wherein a plurality of CCD sensors is used.

Incoming x-radiation 25 causes the scintillator material of the scintillator 9 to luminesce, with some of the triggered photons being collected by the fibers of the fiber-optics transmission element and being conducted to the image zone of the sensor 11. The transmission element consists of a group of individual fibers 26 which are ground at an angle $\alpha$ relative to the transmission direction of the fibers, or alternatively relative to the plane of the scintillator layer 9. The image of the scintillator layer 9 is thus reduced in size on the image zone of the CCD sensor 11 by a factor of sin $\alpha$ of the y-direction. The image in undistorted, however, in the x-direction (perpendicular to the plane of the paper) because the width of the CCD sensor 11 corresponds to the slot width of the secondary diaphragm opening. For example, a decrease in the y-direction from 60 mm to 9 mm results for sin $\alpha$ at about 0.15. With such a detector, therefore, a slot of 7×60 mm can be imaged onto a commercially ayailable CCD sensor having an image zone of 7×9 mm. If, as shown in the embodiment of FIG. 3, two such CCD sensors are disposed above each other, the secondary opening of a standard dental panorama tomograph apparatus can thus be covered. Using this same principle, other formats can be covered, using 1 or 3 or 4 sensors per slot, and by suitable selection of the angle $\alpha$.

Problems which may possibly arise due to light losses can be eliminated by inserting an image intensifier, for example a near-focus image intensifier, between the image zone of the CCD sensor and the adjacent end of the fiber-optics.

As in film systems, the resolution of the system disclosed herein is dependent on the thickness of the luminescent layer. This effect is particularly important in the y-direction, i.e., in the longitudinal extent of the diaphragm opening, because the effective thickness of the luminescent layer in this direction is greater by the factor 1/sin $\alpha$ than the actual thickness.

In order to accommodate this factor, the scintillator layer 9 is not uniform, but is contained within a structure as shown in FIG. 9. The scintillator arrangement has a comb-like or rake-like carrier which defines a plurality of volumns 29, which are filled with scintillator material (not shown) between projectins 28. The carrier 27 is about 100 μm thick, and consists of x-ray permeable material, for example aluminum, plastic or the like. Surfaces 30 of the volumes 29, facing away from the x-rays, are in good optical contact with the end faces of the fibers 26. The remaining surfaces 31 can be mirrored or otherwise reflectively fashioned. This arrangement permits deflection of the optical fibers by nearly 90° from the y-direction toward the z-direction.

As shown in FIG. 8, a radiation shield 32 consisting, for example, of lead, is provided in front of the CCD sensor 11 in the direction of x-ray propagation to protect the sensor 11 from direct exposure to x-rays.

Although modifications and changes may be suggested by those skilled in the art it is the intention of the inventors to embody within the patent warranted hereon all changes and modifications as resonably and properly come within the scope of their contribution to the art.

We claim as our invention:

1. A dental x-ray diagnostics installation for producing panorama tomograms of the jaw of a patient which simulate tomograms obtained by moving x-ray sensitive film behind and past a diaphragm opening at a selected film moving speed, comprising:

radiator meand for generating x-radiation;

detector means for converting x-radiation incident thereon into corresponding light radiation;

a secondary diaphragm diaphragm disposed in front of said detector means having a diaphragm opening which limits dais x-radiation incident on said detector means;

means for supporting said radiator means and said detector means, with said secondary diaphragm, on opposite sides of said jaw and for rotating said radiator means, said secondary diaphragm and said detector means such that x-radiation attenuated by said jaw passes through said secondary diaphragm and is incident on said detector means;

CCD sensor means on which said light radiation is incident for converting said light radiation into electrical signals, said CCD sensor means having an image zone with a plurality of lines in each of which charge is generated corresponding to a portion of said light radiation incident thereon, and having a storage zone to which said charge from said lines is transferred, said liens in combination receiving all of said light radiation to generate a complete charge image corresponding to said x-radiation incident on said detector means;

means for reading out said storage zone; and clock means connected to said CCD sensor means for generating clock pulses at a clock frequency to control the speed of transfer of charge from said lines to said storage zone to store said complete charge image therein, and connected to said means for reading out to control the speed of reading out of said charge image from said storage zone, said clock means generating clock pulses at a clock frequency to transfer charge from said lines to said storage zone and to read out said charge image from said storage zone at a speed selected to simulate said moving film speed.

2. A dental x-ray diagnostics installation as claimed in claim 1, wherein said storage zone of said CCD sensor means is spatially separated from said image zone.

3. A dental x-ray diagnostics installation as claimed inclaim 1, further comprising means for visually displaying said charge image.

4. A dental x-ray diagnostics installation as claimed in claim 1, wherein said image zone has a longitudinal extent divided into a plurality of pixels of length a in the longitudinal direction, and wherein the ratio of said pixel length referenced to said longitudinal segment of said secondary diaphragm opening is $n_x$, and wherein said panorama tomogram simulates a panorama tomogram obtained by moving x-ray-sensitive film past and behind said secondary diaphragm opening at a speed v, and wherein said clock means is further defined by clock means for generating clock pulses at a clock frequency $f_{Takt}$, wherein $$f_{Takt} = \frac{v}{n_x \cdot a}$$

5. A dental x-ray diagnostics installation as claimed in claim 1, wherein said CCD sensor means consists of a single CCD sensor.

6. A dental x-ray diagnostics installation as claimed in claim 1, wherein said CCD sensor means consists of a plurality of CCD sensors, each CCD sensor having an image zone onto which a portion of said light radiation from said detector means is incident, and the respective image zones of said CCD sensors in combination forming said image zone of said CCD sensor means, and receiving all of said light radiation.

7. A dental x-ray diagnostics installation as claimed in claim 1, further comprising:

an image memory; and means for adding the charge of a selected plurality of said lines of said CCD sensor means and entering the sum of said added lines in said image memory.

8. A dental x-ray diagnostics installation as claimed in claim 1, wherein said panorama tomogram simulates a panorama tomogram obtained by moving x-ray-sensitive film behind and past said secondary diaphragm opening at a selected speed, and wherein said clock means is further defined by clock means connected to said CCD sensor means for generating clock pulses at a first clock frequency to control the speed of transfer of charge from said lines to said storage zone to simulate said speed of said moving film, and connected to said means for reading out said storage zone for generating clock pulses at a second frequency higher than said first frequency to control the speed of reading out of said charge image from said storage zone. out of said charge image from said storage zone.

9. A dental x-ray diagnostics installation as claimed in claim 1, wherein said CCD sensor means consists of a plurality of CCD sensors each having an image zone disposed at an angle greater than or equal to 90° relative to the plane of said secondary diaphragm opening, said image zones of said CCD sensors in combination forming said image zone of said CCD sensor means, and further comprising optical coupling means disposed between said detector means and each of said image zones of said CCD sensors.

10. A ental x-ray diagnostics installation as claimed in claim 9, wherein said optical coupling means consists of fiber-optics, said fiber-optics having one end terminating adjacent said respective image zones of said CCD sensors, and an opposite end facing said secondary diaphragm opening and terminating at said angle, said angle being relative to the direction of light transmission in said fiber-optics.

11. A dental x-ray diagnostics installation as claimed in claim 1, wherein said detector means comprises a layer of scintillator material disposed parallel to the plane of said secondary diaphragm opening.

12. A dental x-ray diagnostics installation as claimed in claim 1, wherein said detector means comprises:

a carrier consisting of x-radiation permeable material corresponding in size to the size of said secondary diaphragm opening, said carrier having a plurality of chambers, each chamber having an open side facing said CCD sensor means;

scintillator material disposed in each of said chambers; and means for optically coupling said open side of each of said chambers to said image zone of said CCD sensor means.

13. A dental x-ray diagnostics installation as claimed in claim 12, wherein said secondary diaphragm has a horizontal extent and a vertical extent, wherein said carrier has a comb-like cross section with a plurality of projections, said chambers being formed between respective projections with a horizontal extent corresponding to said horizontal extent of said slot, and being disposed above each other so as in combination to equal said vertical extent of said secondary diaphragm opening.

14. A dental x-ray diagnostics installation as claimed in claim 13, wherein each of said chambers has a plurality of inside surfaces, and wherein said inside surfaces are light-reflective.

15. A method for operating an x-ray diagnostics installation to produce panorama tomograms of the jaw of a patient corresponding to panorama tomograms obtained by moving x-ray sensitive film behind and past a secondary diaphragm opening, said method comprising the steps of:

irradiating the jaw of said patient with x-radiation;

rotating an x-radiation source and an x-radiation detector, with a secondary diaphragm disposed in front of said detector, around the jaw of said patient such that x-radiation attenuated by said jaw and passing through said secondary diaphragm is incident on said detector;

converting the x-radiation incident on said detector into corresponding light radiation;

directing all of said light radiation onto an image zone of at least one CCD sensor to convert said light radiation into electrical signals, said image zone having a plurality of lines in which charge is generated by said light radiation and having a storage zone, said lines in combination generating a complete charge image corresponding to said x-radiation incident on said detector;

transferring said charge from said lines of said image zone to said storage zone at a first clock frequency selected such that the speed of transfer of charge from said lines to said storage zone simulates said speed of said moving x-ray film; and reading out said charge image from said storage zone at a second clock frequency greater than or equal to said first clock frequency.

16. A method as claimed in claim 17, comprising the additional step of visually displaying said charge image.

* * * * *